Figure 1:
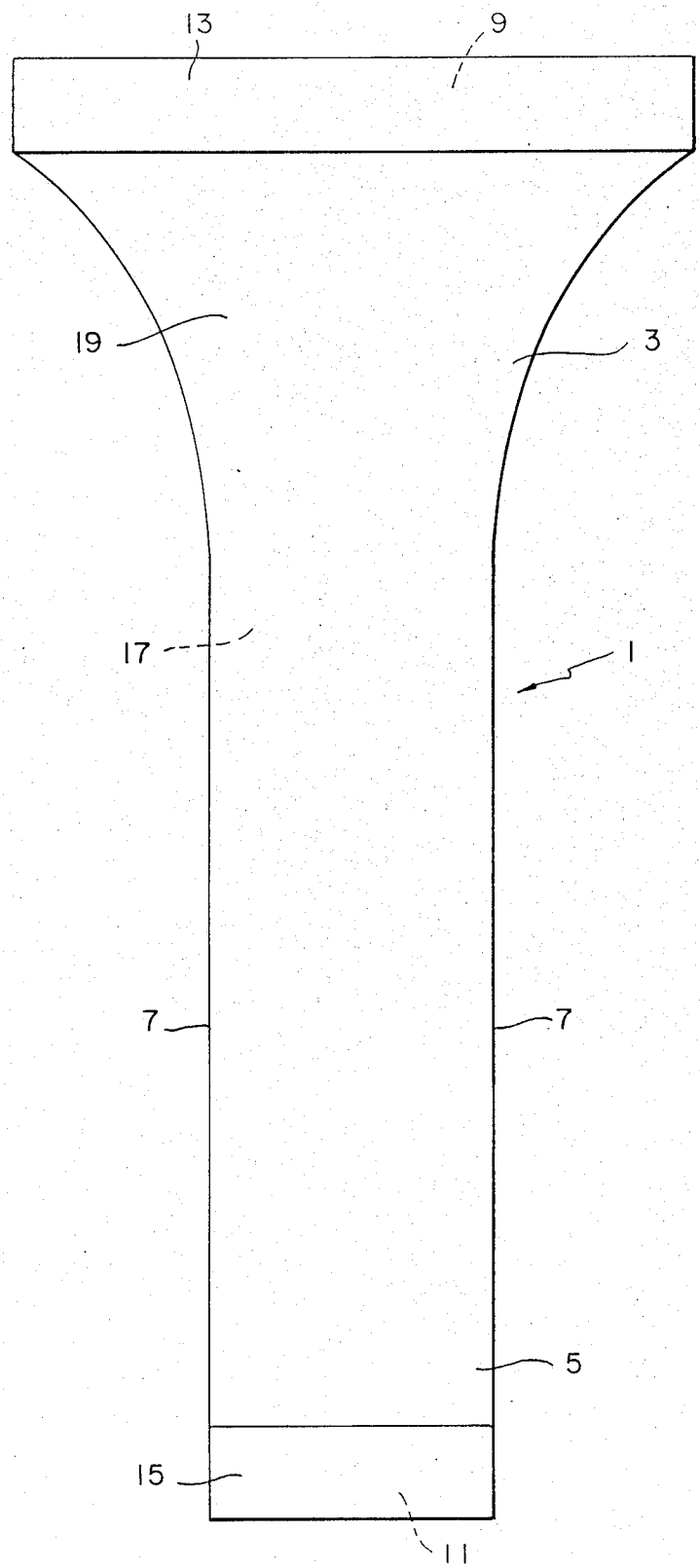

United States Patent [19]

D'Huissier

[11] Patent Number: 4,982,450
[45] Date of Patent: Jan. 8, 1991

[54] PROTECTIVE DEVICE

[76] Inventor: Dominique D'Huissier, 1, Place des Augustins, 1205 Geneva, Switzerland

[21] Appl. No.: 369,131

[22] Filed: Jun. 21, 1989

Related U.S. Application Data

[63] Continuation-in-part of Ser. No. 38,532, Apr. 14, 1987.

[30] Foreign Application Priority Data

May 1, 1986 [CH] Switzerland .................. 01795/86

[51] Int. Cl.$^5$ .......................... A41B 9/00; A41B 9/12
[52] U.S. Cl. .......................................... 2/402; 2/406; 450/81
[58] Field of Search ................ 2/402, 403, 406, 78 R, 2/67; 128/287, 288; 450/81

[56] References Cited

U.S. PATENT DOCUMENTS

| | | | |
|---|---|---|---|
| 2,206,412 | 7/1940 | Levy .................................. | 2/406 X |
| 2,272,830 | 2/1942 | Brady et al. ....................... | 2/406 |
| 2,748,772 | 6/1956 | Titone et al. ...................... | 128/288 |
| 2,891,545 | 6/1959 | Teague .............................. | 2/406 |
| 3,339,208 | 9/1967 | Marbach . | |
| 3,424,162 | 1/1969 | Parravicinini .................... | 128/288 |
| 3,599,640 | 8/1971 | Larson . | |
| 3,929,135 | 12/1975 | Thompson ...................... | 604/385.1 |
| 4,121,305 | 10/1978 | Kolker . | |
| 4,122,552 | 10/1978 | Tedford . | |
| 4,315,508 | 11/1988 | Bolick .............................. | 604/385.2 X |
| 4,343,313 | 8/1982 | Le Jeune ......................... | 450/81 |
| 4,552,795 | 11/1985 | Hansen et al. .................. | 604/358 X |
| 4,553,550 | 11/1985 | Hattori ............................. | 450/81 |
| 4,630,320 | 12/1986 | Van Gompel .................. | 2/406 |
| 4,640,288 | 2/1987 | Hattori ............................. | 128/505 |
| 4,640,859 | 2/1987 | Hansen et al. .................. | 604/385.2 X |
| 4,695,279 | 9/1987 | Steer ................................ | 2/406 X |
| 4,698,855 | 10/1987 | Hicks . | |
| 4,769,283 | 9/1988 | Sipinen et al. ................... | 604/389 X |
| 4,771,483 | 9/1988 | Hooreman et al. ............. | 2/406 X |
| 4,804,380 | 2/1989 | Lassen et al. .................... | 604/378 X |

FOREIGN PATENT DOCUMENTS

| | | |
|---|---|---|
| 3111280 | 9/1982 | Fed. Rep. of Germany . |
| 1580222 | 9/1969 | France . |
| 2302699 | 10/1976 | France . |
| 2409020 | 6/1979 | France . |
| 2429566 | 1/1980 | France . |
| 2481893 | 11/1981 | France . |
| 578845 | 8/1976 | Switzerland . |
| 610736 | 5/1979 | Switzerland . |
| 1144674 | 3/1969 | United Kingdom .................... 2/406 |
| 1198902 | 7/1970 | United Kingdom . |
| 1520740 | 8/1978 | United Kingdom .................... 2/406 |
| 1560925 | 2/1980 | United Kingdom . |
| 2072491 | 10/1981 | United Kingdom . |
| 2155304 | 9/1985 | United Kingdom . |
| 2176692 | 1/1987 | United Kingdom .................... 2/406 |

Primary Examiner—Werner H. Schroeder
Assistant Examiner—Jeanette E. Chapman
Attorney, Agent, or Firm—Young & Thompson

[57] ABSTRACT

A protective device for temporary wear against the skin of a person trying on garments, the device comprising a thin flexible sheet, and pressure-sensitive adhesive at opposite ends of the sheet to hold the sheet temporarily to the skin of a wearer. The sheet is a composite comprised by a an imperforate liquid impervious sheet of polyolefin about 3 to 15$\mu$ in thickness and having bonded thereto on the same side as the adhesive a hydrophilic web of fibers having a diameter of about 5 to 20$\mu$ selected from the group consisting of polypropylene and polyester, the web having a weight of about 10 to 30 g/m$^2$.

10 Claims, 1 Drawing Sheet

PROTECTIVE DEVICE

This application is a continuation-in-part of my co-pending application Ser. No. 07/038,532 filed Apr. 14, 1987.

When trying on clothing and particularly bathing suits, bathing pants, underwear, slips, pants or fine lingerie, etc., there is always a hygienic and aesthetic problem. Thus for hygiene, it is necessary to keep on at least a slip when trying on new clothing, which frequently, particularly when trying on bathing suits or fine lingerie, prevents normal appraisal whether the piece tried on fits perfectly or not because the slip which has been kept on itself modifies the silhouette particularly by printing lines, folds or thickened portions through the clothing that is being tried.

Many people are thus tempted to try on garments without protection, directly on their skin, to the detriment of cleanliness, particularly when the garment is not ultimately bought. Moreover, the protection offered by a slip which one keeps on is quite chancy because this slip may itself not be entirely clean and is not impervious to liquid.

The present invention aims to overcome the recited drawbacks and has for its object a disposable protective device, for a single use, which is described in greater detail hereafter.

The accompanying drawing shows schematically and by way of example an embodiment of the device according to the invention.

Referring now in greater detail to the drawing, there is shown a protective device 1 according to the present invention, of generally T-shaped configuration, having a widened end 3 and a narrow end 5 bordered by longitudinal edges 7 that are concave at end 3, which is to say over a minor portion of the length of the device, and straight over the rest of the length of the device.

Device 1 is of thin sheet material to be described in greater detail hereafter and is adapted to be temporarily worn by the user when trying on a garment to see whether it fits. It is to be applied to the bare skin of the user, and to be fitted between the legs of the user, and for this purpose is provided with a relatively long adhesive strip 9 along end 3 and a relatively short adhesive strip 11 along end 5. Adhesive strip 9 is covered by a protective paper 13 and adhesive strip 11 is covered by a protective paper 15, these protective papers being adapted to be peeled off so as to leave exposed the respective adhesive strips for direct application to the skin of the user for as long as the protective device is needed. Of course, once the fitting has been completed and the protective device is no longer needed, the user will simply peel off the adhesive strips 9 and 11 from her skin, leaving behind no adhesive residue, because the adhesive used has a greater adhesion for the material of the device 1 than for the skin of the user.

The device 1 is of thin flexible sheet material of very light weight, which is liquid impervious but which has a liquid-absorbent surface adjacent the user, that is, on the same side as adhesive strips 9 and 11 and protective papers 13 and 15, which is to say the side of the device 1 which is visible in the drawing.

The device 1 is accordingly characterized by a thin flexible very tough sheet of polyolefin 17 which is on the side of the device adapted to be away from the wearer when the device is worn, and a liquid absorptive layer 19 on the same side as the wearer, which is the side visible in the drawing.

Layer 17 has a thickness between 3 and 15μ, preferably between 5 and 10μ. It is imperforate and liquid impervious and can be of polyethylene, but is preferably of an ionomer comprised of relatively short polyethylene chains and granules of polymethacrylate linked with sodium ions, i.e. a sodium-based ethylene-methacrylate copolymer, among which are particularly preferred those DuPont products known as "Surlyn" most particularly "Surlyn 1652".

The material of layer 17 is thermoplastic and is preferably formed into the required thin film by melt extrusion.

For the layer 19 is used a spun web of fibers of polypropylene or polyester, preferably polypropylene, whose fibers have been hot calendered and thus thermobonded together. Layer 19 has a weight of 10 to 30 g/m$^2$, preferably about 20 g/m$^2$. The fibers have a diameter of 5 to 20μ, preferably 10 to 15μ.

Despite the fact that layer 19 is of polypropylene or polyester, it is nevertheless hydrophilic, because of the small diameter of its fibers.

To assemble layers 17 and 19, the thermobonded calendered spun fiber layer 19 is laid on layer 17 just after the melt extrusion of layer 17, when layer 17 has a temperature from 260° to 300° C. The composite material thus produced can then be rolled up into a roll, which provides sufficient pressure between the layers 17 and 19 to bond them together. Alternatively, the composite of layers 17 and 19 can be calendered between rolls, just as was the spun fiber layer 19 itself.

The layers 9 and 11 of adhesive can then be applied on the spun fiber side of the composite, and for this purpose any pressure-sensitive adhesive suitable to adhere releasably to human skin is usable, e.g. 3M's MSX 678 PSL HL 10150012. A suitable adhesive has greater adhesion for device 1 than for human skin and so leaves no residue on the skin upon removal.

The papers 13 and 15 are then applied, which have on the side contacting the adhesive a release layer of silicone resin which has greater adhesion for the paper than for the adhesive.

The use of this protective device is extremely simple. It is placed between the legs with the wider end 3 in front and the layer 19 against the bare skin of the user. Preferably, of course, the papers 13 and 15 are removed only one at a time and the freshly-exposed adhesive is applied first to one side of the user's body and then to the other. Layer 9 should be applied horizontally at the base of the user's stomach and layer 11 at the rear of the body, adjacent the coccyx.

The device is very cheap, whereby the device can be given free to users at the point of sale of clothing. Automatic distributors of these devices can even be provided.

It is evident that the devices can be made in several sizes to satisfy the needs of all the clientele.

Finally, the device can obviously bear advertising, particularly the trademarks of clothing.

The device can be translucent or opaque and can also be colored, preferably with a skin color, so as not to change the apparent color of a garment which is tried on over the device.

The device is thus able to absorb a few drops of moisture and does not adhere to the skin except where adhesive is provided for this purpose and so has a smooth and pleasant feel against the skin.

Of course, once the device is removed from the body of the wearer, it is simply discarded.

Although the present invention has been described in connection with preferred embodiments, it is to be understood that modifications and variations may be resorted to without departing from the spirit of the invention, as those skilled in this art will readily understand. Such modifications and variations are considered to be within the purview and scope of the present invention as defined by the appended claims.

What is claimed is:

1. A device for protecting garments that are being tried on, the device comprising a thin flexible sheet adapted to be worn temporarily against the skin of the user, pressure-sensitive adhesive at opposite ends or one side of the sheet to hold the sheet temporarily to the skin of the user, the sheet being a composite comprised of an imperforate liquid impervious sheet of polyolefin about 3 to 15$\mu$ in thickness and having bonded thereto on the same side as the adhesive and over substantially all the area of the sheet a hydrophilic web of fibers having a diameter of about 5 to 20$\mu$ selected from the group consisting of polypropylene and polyester, said web having a weight of about 10 to 30 g/m$^2$.

2. A device as claimed in claim 1, in which the material of said sheet is a ionomer.

3. A device as claimed in claim 2, in which said ionomer is a sodium-based copolymer of polyethylenes and polymethacrylate.

4. A device as claimed in claim 1, in which said sheet has a thickness of about 5 to 10$\mu$.

5. A device as claimed in claim 1, in which said web has a weight of about 20 g/m$^2$.

6. A device as claimed in claim 1, in which said web fibers have a thickness of about 10 to 15$\mu$.

7. A device as claimed in claim 1, in which the fibers of said web are thermobonded to each other.

8. A device as claimed in claim 1, in which said web is thermobonded to said sheet.

9. A device as claimed in claim 1, in which said fibers are bonded to said sheet and to each other.

10. A device as claimed in claim 1, said pressure-sensitive adhesive being applied as a layer of adhesive on said fibers.

* * * * *